United States Patent
Bendera et al.

(10) Patent No.: US 9,333,184 B2
(45) Date of Patent: *May 10, 2016

(54) COMPOSITION AND METHOD FOR AFFECTING MALE AND FEMALE HORMONE LEVELS

(71) Applicant: NOKOMIS RESEARCH, INC., Scottsdale, AZ (US)

(72) Inventors: Richard J Bendera, Scottsdale, AZ (US); Leanna S Wilson, Scottsdale, AZ (US)

(73) Assignee: NOKOMIS RESEARCH, INC., Carefree, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,242

(22) Filed: Dec. 3, 2012

(65) Prior Publication Data

US 2014/0155492 A1   Jun. 5, 2014

Related U.S. Application Data

(60) Provisional application No. 61/566,647, filed on Dec. 3, 2011.

(51) Int. Cl.
*A61K 31/132* (2006.01)

(52) U.S. Cl.
CPC .................................... *A61K 31/132* (2013.01)

(58) Field of Classification Search
CPC ...................................................... A61K 31/132
See application file for complete search history.

(56) References Cited

U.S. PATENT DOCUMENTS 6,555,140 B1   4/2003   Bendera et al.

OTHER PUBLICATIONS

ZRT Laboratory, Dec. 23, 2013, pp. 1-26.*
Dr. Frank Sweet, M.D. and N.D. Medical assessment of Eroxil and Erosyn Jul. 7, 2005.
www.desbio.com Health Talk Xyocel: The Key to Restoring Youthful Vitality Mar. 2007, published by Desert Biologicals.
Nokomis Research Inc. www.nokomisresearch.com New Product Introduction Jun. 5, 2006.

* cited by examiner

*Primary Examiner* — Kendra D Carter
(74) *Attorney, Agent, or Firm* — Weiss & Moy, P.C.; Veronica-Adele R. Cao

(57) ABSTRACT

A composition and method for enhancing fertility of a male or female human by affecting levels of cortisol, dehydroepiandrosterone sulfate, testosterone, progesterone, and estradiol in the human. The composition comprises effective amounts of spermine and spermidine, administered at least once daily for a period of at least thirty days.

12 Claims, 1 Drawing Sheet

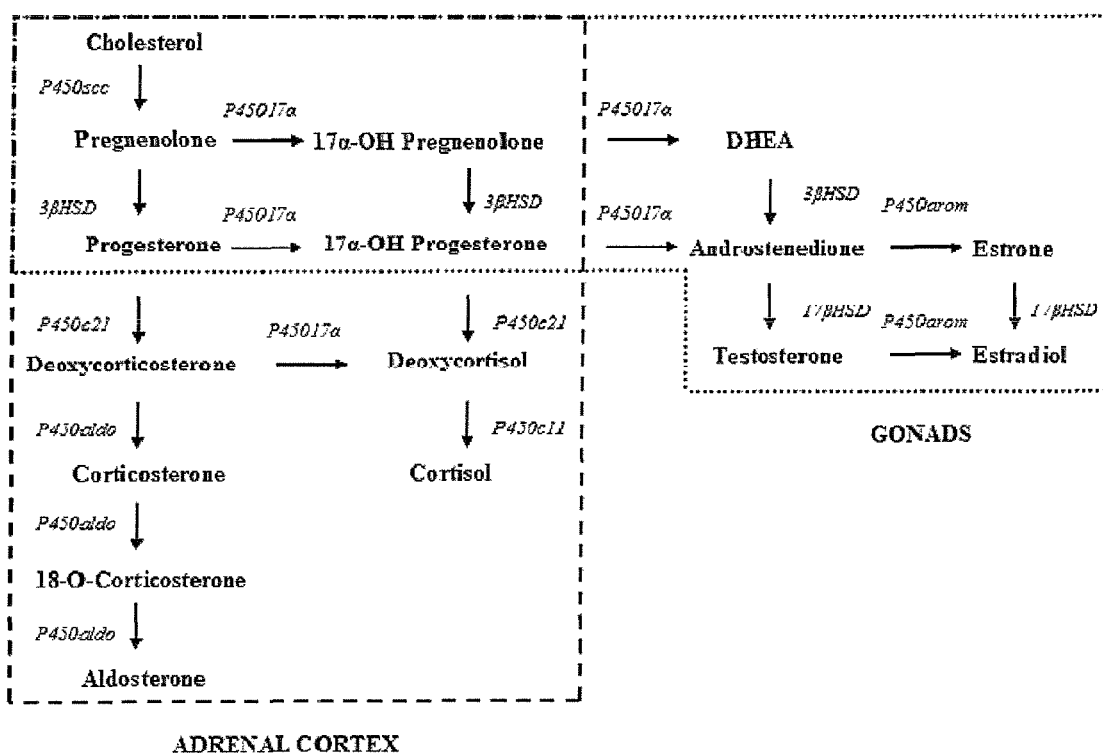

COMPOSITION AND METHOD FOR AFFECTING MALE AND FEMALE HORMONE LEVELS

CROSS-REFERENCE TO RELATED APPLICATION

This disclosure claims priority to U.S. Provisional Application Ser. No. 61/566,647 titled COMPOSITION AND METHOD FOR RESTORING, REGULATING AND BALANCING MALE AND FEMALE ESTROGEN BALANCE, which was filed on Dec. 3, 2011 in the names of the Applicants herein. This disclosure is also related to U.S. Pat. No. 6,555,140 issued on Apr. 29, 2003 to the applications of the present invention.

FIELD OF THE INVENTION

This disclosure generally relates to the field of hormonal balancing, and more particularly, to a composition and method for affecting mammalian male and female hormone levels.

BACKGROUND OF THE INVENTION

Researchers have concluded that an overabundance of estrogen is responsible for a vast number of today's health problems. This overabundance of estrogen is referred to as "estrogen dominance" and is an increasingly serious problem for both women and men. Some researchers believe that estrogen dominance is the primary cause of prostate enlargement and prostate cancer in men and a big risk factor for breast cancer in women.

Estrogen dominance can occur during the aging process and can also occur from exposure to estrogen-like substances in the environment known as "xenoestrogens."

Xenoestrogens are synthetic substances that differ from those produced by living organisms and that imitate or enhance the effect of estrogens. The estrogenic stimulation is an unintended side-effect of these agents or their metabolites. Xenoestrogens are part of a heterogeneous group of chemicals that are hormone or endocrine disrupters. They differ from phytoestrogens (estrogenic substances from plants), mycoestrogens (estrogenic substances from fungi), and pharmacological estrogens (estrogenic action is intended). External estrogens from a variety of sources may have a cumulative effect upon living organisms, and xenoestrogens may be part of a larger picture of a process of estrogenization of the environment. Xenoestrogens have only been recently (less than 70 years) introduced into the environment, as produced by industrial, agricultural, and chemical companies.

Xenoestrogens have been implicated in a variety of medical problems. Foremost is the concern that xenoestrogens, as false messengers, disrupt the process of reproduction. Studies have implicated observations of disturbances in wildlife with estrogenic exposure. Reproductive issues, which are of concern in humans, are fetal exposure (perhaps leading to hypospadias) and decreased reproductive ability in men (i.e. decrease in sperm numbers). Another issue is the potential effect of xenoestrogens as oncogenes, specifically in relation to breast cancer.

Xenoestrogen environmental sources includes: commercially raised meat (beef, chicken and pork), canned foods, plastic food wraps, plastic drinking bottles, STYROFOAM cups, personal care products, cosmetics, birth control pills and spermicides, detergents, all artificial scents (air fresheners, perfumes, etc), pesticides and herbicides, paints, lacquers and solvents.

There are three basic estrogens: E3 (estriol), the least powerful and most beneficial, comprising 80-90% of human estrogen; E2 (estradiol), the most powerful and most carcinogenic; and E1 (estrone), which has similar properties to estradiol, but is considerably less biologically active. As men age, their levels of estrogen rise, especially the levels of estrone and estradiol, which are the two most dangerous and potent estrogens. This phenomenon is now identified as "andropause". A man over 50 years of age literally has more estrogen than a postmenopausal woman. The prostate is embryologically the same as the uterus in females: and research studies have shown that, like the uterus, when prostate cells are exposed to excess estrogen, the cells proliferate and become cancerous. In fact it is becoming clear that the excess of estrogen in aging men is responsible for a variety of problems such as adiposity, breast development, many cancers, prostate problems, baldness and many other problems commonly associated with advanced age.

Men also produce progesterone, but only about half the amount that females do. During the aging process, progesterone levels in men fall, especially after age 60. Progesterone is the primary precursor of the male hormone testosterone, which is an antagonist to estradiol (E2) and a protector against certain types of cancer. Progesterone is vital to good health in both men and women.

The concurrent increase of estrogen levels and decrease of progesterone levels create a very serious hormonal imbalance that is very unhealthy. Either one of these hormonal level changes alone would be bad enough, but both changes occurring together leads to a vicious cycle.

Because progesterone is the chief inhibitor of an enzyme called 5-alpha reductase that is responsible for converting testosterone to dihydrotestosterone (DHT), when the level of progesterone falls in men, the amount of conversion from testosterone to DHT increases. Increased levels of DHT lead to prostate enlargement and also an increased risk of cancer due to the decreased cancer protection that testosterone provides.

As the level of DHT increases (and testosterone decreases), the relative level of estradiol in men increases. This is compounded by the fact that there are inadequate amounts of progesterone present to exhibit its counteracting effect of stimulating the P53 cancer protection gene.

Like perimenopausal women, men experience a tendency to gain weight in midlife. Rising estrogen production can result because fat cells contain the aromatase enzyme that converts testosterone into estrogen. Unmetabolized estrogen creates a vicious cycle resulting in further estrogen production. This occurs because fat is one source of more active aromatase enzymes, causing further estrogen production and weight gain.

It is common for women to experience surges of abnormally high estrogen levels during menopausal and premenopausal periods, as well as earlier in life. It is believed that an excess of estrogen, coupled with a deficiency of progesterone (the counter hormone to estrogen), is the common denominator for a lot of female troubles.

Some women will develop the estrogen dominance syndrome much later in life, sometimes as a result of diet, liver impairment, or environmental factors or also as a result of anovulatory cycles before menopause—that is, menstrual cycles in which no ovulation has occurred. Ovulation is necessary in order to produce the corpus luteum, (which means "yellow body") that is found on the surface of the ovary after ovulation. Surrounding the ripening egg, the corpus luteum remains after ovulation to produce progesterone for the last half of the menstrual cycle. Without ovulation, less progesterone is produced, which can cause estrogen imbalance in some women. Diseases or problems that are thought to be related to or affected by excess estrogen and deficient progesterone in women and men are: accelerated aging process; allergies; autoimmune disorders; breast cancer; cold hands and feet; decreased sex drive; depression; dry eyes; infertility; uterine cancer; fat gain in abdomen, hips, and thighs; fatigue; fibrocystic breast disease; hair loss; headaches; hypoglycemia; increased blood clotting; early onset of menstruation; menstrual disturbances (irregular and heavy bleeding); endometriosis (disorder of uterine tissue); insomnia; foggy thinking and memory loss; mood swings; ovarian cysts; premenopausal bone loss; prostate cancer; sluggish metabolism; thyroid dysfunction; uterine cancer; uterine fibroids; water retention; and bloating.

SUMMARY

This summary is provided to introduce a selection of concepts in a simplified form that are further described below in the DESCRIPTION OF THE DISCLOSURE. This summary is not intended to identify key features of the claimed subject matter, nor is it intended to be used as an aid in determining the scope of the claimed subject matter.

In accordance with aspects of the present disclosure, a composition for affecting hormone levels of a mammal is disclosed. The composition comprises effective amounts of spermine and spermidine.

In accordance with another aspect of the present invention, a method of affecting hormone levels of a mammal is disclosed. The method comprises the steps of: providing a composition that comprises between approximately 2.5 mg and 2.7 mg spermine and between approximately 2.5 mg and 2.7 mg spermidine; and administering the composition to the mammal.

In accordance with another aspect of the present invention, a method of a method for increasing fertility in a mammal is disclosed. The method comprises the steps of: providing a composition that comprises between approximately 2.5 mg and 2.7 mg spermine and between approximately 2.5 mg and 2.7 mg spermidine; administering the composition to the mammal at least once daily for a period of at least thirty days; and affecting levels of at least one of cortisol, dehydroepiandrosterone sulfate, testosterone, progesterone, and estradiol in the mammal.

BRIEF DESCRIPTION OF THE DRAWINGS

The novel features believed to be characteristic of the application are set forth in the appended claims. The application itself, however, as well as a preferred mode of use, further objectives and advantages thereof, will be best understood by reference to the following detailed description of illustrative embodiments when read in conjunction with the accompanying drawing, wherein:

FIG. 1 is a diagram showing hormone production as it occurs in a mammal.

DESCRIPTION OF THE DISCLOSURE

The description set forth below is intended as a description of presently preferred embodiments of the disclosure and is not intended to represent the only forms in which the present disclosure can be constructed and/or utilized. The description sets forth the functions and the sequence of steps for constructing and operating the disclosure. It is to be understood, however, that the same or equivalent functions and sequences can be accomplished by different embodiments that are also intended to be encompassed within the spirit and scope of this disclosure.

While there have been some treatments proposed for treating estrogen dominance, none have been entirely successful, and there remains a need for identifying improved and/or alternative therapies for treating these disorders. In particular, improved methods and compositions should be effective and efficiently delivered in a non-invasive manner, have minimum side effects and optionally be compatible with other hormonal treatments.

Spermine and spermidine are found in virtually every cell in the body. Both of these vital polyamines are found in plant, meat and fish sources, with higher levels of spermidine found in vegetables and strangely high amounts of spermine being found in meats and fish.

A chemical analysis has been performed in respect of corn, namely the chemical constituents of *Zea mays* L. (Poaceae); cucumber, namely the chemical constituents of *Cucumis sativus* L. (Cucurbitaceae); oats, namely the chemical constituents of *Avena sativa* L. (Poaceae); and radishes, namely the chemical constituents of *Raphanus sativas* L. (Brassicaceae) (The Clinicians' Handbook of Natural Healing by Gary Null, Kensington Publishing, New York, 1997). Over ninety different chemicals and compounds were identified in the list of constituents. The present invention discloses that spermine and spermidine are the constituents that are capable of restoring balanced hormonal levels in male and female humans.

Spermine and spermidine are both known as polyamines. Polyamines are organic cations of low molecular weight which are present in prokaryotic and eukaryotic cells. The major polyamines in mammals are putrescine, spermidine, and spermine (Colandra et al. p. 46:209-222, (1996) Apptla).

Polyamines are ubiquitous chemicals that occur in every living cell. They fulfill an array of roles in cellular metabolism and are involved in many steps of protein, RNA and DNA synthesis, from the control and initiation of translation to the regulation of its fidelity (Dunshea and King, p. 73:819-828 (1995))]. There is a scarcity of information on the bioavailability and mechanism of polyamine uptake by the gut and the fate of polyamines derived from the gut rumen in humans (Dunshea and King, p. 73:819-828 (1995)). It appears that polyamines can be readily taken up from the gut rumen, and it has been suggested that this occurs by pass of diffusion (Dunshea and King, p. 73:819-828 (1995)).

Polyamines have different patterns of tissue distribution between mammalian species and age and different hormone and environmental conditions will influence the polyamine pool (Colandra et al., p. 46:209-222 (1996) Apptla).

Biogenic amines exist naturally in many food stuffs and vegetables such as Chinese cabbage, endive, iceberg lettuce, and radishes all of which have been found to contain varying levels of the aforementioned polyamines. However, changes in the biogenic amine content from ungerminated seeds to young plants show a reduction in concentration of these polyamines. Furthermore, it is not clear how such polyamines could be released from the aforementioned plants.

Both spermine and spermidine, when ingested, are transported from inside the intestine into the blood stream with only 30% of the ingested amount being metabolically degraded. Therefore about 70% of what is ingested is metabolically available for the body to use in various cellular processes.

Both spermine and spermidine are essential for healthy cell development in the human body (Merck Index). Accordingly, the present invention discloses a composition and method wherein effective amounts of spermine and/or spermidine are used to affect hormone levels in both human males and females; e.g. restoring balanced hormonal levels (e.g. cortisol, dehydroepiandrosterone sulfate, testosterone, progesterone, and estradiol) for both males and females with estrogen dominance. Spermidine and spermine are naturally derived from green plant materials. Although it is possible to produce synthetic or recombinant spermine, and spermidine, it is preferably derived from corn, cucumber, oats, lettuce, lentil seeds, radish leaves, radish seeds, cabbage, various meats and fish. Nonetheless, it should be clearly understood that spermine and spermidine, as disclosed herein, may comprise the compounds as isolated from corn, cucumber, oat, and radish leaves and stems, or any other natural source, but may also include any portion of the compounds which provide the biological activity of restoring balanced hormonal levels in human males and human females who have estrogen dominance. It should also be clearly understood that spermine and spermidine may include any and all synthetic analogs of the naturally occurring polyamines, or biologically active portions thereof, howsoever prepared.

Where a human male or a human female is the subject, the composition may comprise a combined dose of approximately 5 mg-5.4 mg; i.e. between approximately 2.5 mg-2.7 mg of spermine and between approximately 2.5 mg-2.7 mg of spermidine. It should be clearly understood, however, that the dosages of the active substances of the compositions disclosed herein may vary depending on many factors such as pharmacodynamic characteristics of the particular substance and its mode and routes of administration; source of substance; age, health, and weight of the patient; nature and extent of symptoms; kind of current treatment; frequency of treatment; and the effect desired.

The composition of the present invention, when administering spermine and spermidine, preferably contains suitable pharmaceutical carriers or diluents as appropriate. Other herbals may be added to fulfill the requirements of a homeopathic formula. Suitable pharmaceutical carriers and methods of preparing pharmaceutical dosage forms are described in Remington's Pharmaceutical Sciences, Mack Publishing Company, Veterinary Drug Handbook, Donald C. Plum, University of Minnesota, and Canadian Compendium of Veterinary Products, Canadian Animal Health Institute, 6th Ed., North American Compendium Ltd., Hensal, Ontario, which is a standard of reference in this field. Suitable pharmaceutical diluents, excipients, or carriers may be suitably selected with respect to the intended form of administration, that is, oral tablets, capsules, elixirs, syrups, teas, paste, and the like, and would be consistent with conventional pharmaceutical practices. Routes of administration may include oral, transdermal, and injection by intravenous, intramuscular or subcutaneous routes. A person skilled in the art would readily ascertain what a suitable pharmaceutical carrier would be.

EXAMPLES

The incidence and prevalence of infertility and sexual dysfunction in men and women is increasing. The biogenic polyamines spermine and spermidine are important for sexual function as well as fertility. Spermine and spermidine are present in plant foods and are synthesized from ornithine and methionine in mammals. Stress and stress-associated hormone disruption are contributors to both poor sexual function and infertility. Spermine and spermidine are important in reducing the impact of stress on living organisms.

An study was designed to observe the impact of spermine and spermidine supplementation of hormone levels of otherwise healthy human subjects with no history of infertility or sexual dysfunction. Pre- and Post-supplement levels of cortisol, dehydroepiandrosterone sulfate (DHEAS), testosterone, progesterone, and estradiol as well as 30-day post-supplement levels of these hormones were performed on age/gender equivalent subjects.

Clinically significant reductions in cortisol were seen in 30 days among 83% of male participants and 37% of female participants. 66% of male participants maintained lower cortisol levels 30 days after withdrawal of the study supplement. In women, the cumulative effect of the spermine and spermidine supplementation continued with 50% reporting a significant reduction in cortisol levels 30 days after withdrawal of the study supplement. There was an average of 3.3 pounds of weight loss during the first 30 days of supplementation without any dietary or metabolic intervention.

Furthermore, 7 out of 8 female participants demonstrated a moderate increase in DHEAS at 30 days, while 5 of 7 male participants demonstrated a significant DHEAS increase in 60 days. 83% of men had a decrease in estradiol and 100% of men had a decrease of progesterone at 30 days while 75% of women in follicular phase of the menstrual cycle experienced both an increase in estradiol and a significant increase in progesterone. In men of the under 50 year age group testosterone levels increased by an average of 48.9% (28.3 pg/mL) while in the over 50 age group testosterone levels decreased by an average of 36.7% (33 pg/mL). In women, 75% had an average increase of 48.8% (10.6 pg/mL) in testosterone levels at 30 days while the same number (75%) had an average decrease of 32.7% (10.5 pg/mL) in testosterone levels at 60 days.

For both fertility and sexual performance it is important to reduce cortisol levels. Also important to fertility is the balancing of various hormone ratios during reproductive years. Likewise, it is important for sexual performance of women post-menopause and men post-androupause to achieve cortisol reduction and hormone balance. The biogenic polyamines spermine and spermidine show a trend toward hormone balance.

The biogenic polyamines spermine and spermidine are ubiquitous in plants since they are part of prokaryotic and eukaryotic stress response. They are present in mammalian tissues as well. In humans and other mammals, spermine and spermidine are synthesized from the amino acids ornithine and methionine (Groppa & Benevides (2008); Loser C. et al., p. 84:S55-8 (2000); Tabor C W et al., p. 53:749-90 (1984); Loser C., p. 54:213-23 (1993); and H. G. Williams, p. 171: 882-894 (1970). It has also been reported that spermine and spermidine participate with nitric oxide synthesis, making spermine and spermidine critical to reproduction. Salts of spermine have also been isolated in seminal fluid (Bardocz S. et al., p. 73:819-28 (1995)).

Polyamines provided by food seem to be essential for the maintenance of normal growth and maturation (Dandrifosse G, Peulen O., et al., p. 59:81-6 (2000); and Dufour C, et al., p. 95:112-6 (1988)). Dietary polyamines are associated with cellular growth and differentiation. This association was reported to be due to polyamine interaction with DNA, RNA, and proteins (Loser C., et al., p. 84:S55-8 (2000); and Dufour, C., et al., p. 95:112-6 (1988)). Furthermore, exogenous polyamines modulate mucosal proliferation and absorption from diet (Bardocz S., p. 6:341-6 (1995)). Hence, insufficient polyamine intake could hinder important health enhancing effects of polyamines such as induction of tolerance to dietary allergens (Lovaas, E, et al., p. 11:455-61 (1991)). A high intake of spermine is associated with a decreased risk of food allergy among suckling rats as well as in children, due to the contribution of spermine to maturation of both the immune system and the small intestinal mucosa (Tabor C W, et al., p. 53:749-90 (1984); Exton M S, et al., p. 61:280-9 (1999); and Exton N G, p. 25:187-99 (2000)).

Dietary polyamines provide both antioxidant and anti-inflammatory properties (Loser, C., et al., p. 44:12-6 (1999); and Sabater-Molina, M., et al., p. 23:87-95 (2007)). The antioxidant activity of polyamines has been shown to be even stronger than that of some antioxidant vitamins (Loser, C., et al., p. 44:12-6 (1999); and Sabater-Molina, M., et al., p. 23:87-95 (2007)).

Example 1

Cortisol

Glucocorticoids, primarily cortisol, are produced by the adrenal glands in response to stressors such as emotional upheaval, exercise, surgery, illness or starvation. In response to a stressor, most organisms have an automatic reaction that engages the mechanisms necessary for mobilization. This response, automatically activated as a defense against any threat, is designed to provide the energy resources necessary for survival and to shut down all unnecessary functions, such as digestive and reproductive functions. Consequently, in order for an organism to engage in sexual activity, the stress response would need to be inactive.

Cortisol plays an essential role in the stress response. Although there are a series of autonomic and endocrine responses that occur when an organism is faced with a stressor, cortisol has become commonly known as "the stress hormone." Cortisol's role in the endocrine system is metabolic, and it is released both after eating and in response to stressful situations. As part of the stress response, cortisol acts on various metabolic pathways to provide energy where it is needed in the body during a stressful fight or flight situation.

Although increased cortisol release is not the only marker of the stress response, measuring cortisol response is a simple way to make a reasonable judgment about whether or not an organism is experiencing a stress response. This is particularly useful in sexual arousal studies because cortisol is only active in specific instances, whereas, for example, the sympathetic nervous system is activated in a variety of situations including both sexual arousal and during stress. (Eliassen, K A, et al., p. 78:273-80 (2002); Igarashi K., et al., p. 271:559-64 (2000); and Deloyer P., et al., p. 13:1027-32 (2001)).

Cortisol is made from progesterone. (See Table 1). In situations where there is excessive cortisol production and release in response to stress, progesterone levels decline. This happens because cortisol is much more necessary for life than progesterone, therefore progesterone gets converted into cortisol. Since cortisol and progesterone compete for common receptors in the cells, cortisol impairs progesterone activity, setting the stage for estrogen dominance. Without adequate progesterone, a fertilized egg will not be maintained in the uterus. According to the American Society for Reproductive Medicine, infertility affects about 10% of men and women of childbearing age. Chronically elevated cortisol levels can be a direct cause.

TABLE 1

Baseline Patient Characteristics

| | (n = 15) | Cortisol | DHEAS | Testosterone | Progesterone | Estradiol |
|---|---|---|---|---|---|---|
| Age, y | 37.1 | 7.1 | 6.8 | 48.9 | 30.3 | 2.2 |
| Men | 42.8 | 7.8 | 13.7 | 71.7 | 23.1 | 1.9 |
| Women | 32.2 | 6.8 | 7.5 | 29.0 | 36.5 | 2.0 |

*Data are presented as mean (%) values, unless otherwise indicated.

In this study, 83% of men and 37% of women experienced a significant reduction in cortisol during the 30-day supplementation with spermine and spermidine. Once the supplement was withdrawn, the levels of cortisol began to rise among men but continued to decline among women, reaching 50% after an additional 30 days. (See Table 2, 3).

TABLE 2

Male Cortisol Levels
Cortisol

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 7.3 | 7.6 | 9.1 | 0.3* | 4.1%* | 1.5 | 19.7% | 1.8 | 24.7% |
| 6.4 | 3.0 | 3.2 | -3.4 | -53.1% | 0.2 | 6.6% | -3.2 | -50.0% |
| 8.1 | 7.1 | 12.5 | -1.0 | -12.3% | 5.4 | 76.1% | 4.4 | 54.3% |
| 5.6 | 2.8 | 1.2 | -2.8 | -50.0% | -1.6* | -57.1%* | -4.4 | -78.6% |
| 8.2 | 4.4 | 18.3 | -3.8 | -46.3% | 13.9 | 315.9% | 10.1 | 123.1% |
| 8.28* | 0.9 | 3.8 | -7.3 | -89.0% | 2.9 | 322.0% | -4.4 | -53.7% |
| 10.8 | *** | 4.4 | *** | *** | *** | *** | -6.4 | -59.3% |
| Mean Increase: | | | -3.7 pg/mL | -50% | * | * | -4.6 pg/mL | -60% |
| Mean Decrease: | | | * | * | 4.8 pg/mL | 148.1% | 5.4 pg/mL | 67.4% |

*Only 1 participant met this criterion
***Participant unavailable

TABLE 3

Female Cortisol Levels
Cortisol

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 9.6 | 9.9 | 6.7 | 0.3 | 3.1% | -3.2 | -32.3% | -2.9 | -30.2% |
| 6.0 | 7.1 | 13.1 | 1.1 | 18.3% | 6.0 | 84.5% | 7.1 | 118.3% |
| 3.5 | 1.9 | 1.0 | -1.6 | -45.7% | -0.9 | -47.4% | -2.5 | -71.4% |
| 10.7 | 0.8 | 0.8 | -9.9 | -92.5% | 0.0 | 0.0% | -9.9 | -92.5% |
| 7.9 | 8.9 | 9.1 | 1.0 | 12.7% | 0.2 | 2.2% | 1.2 | 15.2% |
| 6.1 | 2.3 | 1.8 | -3.8 | -62.3% | -0.5 | -21.7% | -4.3 | -70.5% |
| 2.0 | 4.3 | 3.4 | 2.3 | 114.9% | -0.9 | -20.9% | 1.4 | 70.0% |
| 6.1 | 8.4 | 14.0 | 2.3 | 37.7% | 5.6 | 66.6% | 7.9 | 129.5% |
| | Mean Increase: | | -5.1 pg/mL | -66.8% | -1.4 pg/mL | -30.6% | -4.9 pg/mL | -66.2% |
| | Mean Decrease: | | 1.4 pg/mL | 37.3% | 3.9 pg/mL | 51.1% | 4.4 pg/mL | 83.3% |

Example 2

DHEAS

DHEA, or dihydroepiandrosterone, is one of the major steroid hormones produced by the adrenal glands, and sometimes by the gonads (ovaries and testes). The body converts DHEA into male and female sex hormones, such as estrogen and testosterone. When a sulfate group (a special molecule containing a sulfur atom and four oxygen atoms) is added to DHEA, it forms DHEAS (dihydroepiandrosterone sulfate). Most DHEA is found as DHEAS in the blood. Women with infertility and men with erectile dysfunction frequently have low levels of DHEAS.

In this study, 42.8% of men at 60 days and 87.5% of women at 30 days experienced a significant elevation in DHEAS following 30 day supplementation with spermine and spermidine. (Table 4, 5).

TABLE 4

Male DHEAS Levels
DHEAS

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 8.7 | 14.3 | 10.4 | 5.6* | 64.4%* | -3.9 | -27.3% | 1.7 | 19.5% |
| 42.2 | 3.9 | 9.8 | -38.3 | -90.8% | 5.9 | 151.3% | -32.4 | -76.8% |
| 5.1 | 4.0 | 4.5 | -1.1 | -21.6% | 0.5 | 12.5% | -0.6 | -11.8% |
| 10.1 | 5.9 | 4.5 | -4.2 | -41.6% | -1.4 | -23.7% | -5.6 | -55.4% |
| 3.6 | 2.8 | 4.2 | -0.8 | -22.2% | 1.4 | 50.0% | 0.6 | 16.7% |
| 6.9 | 1.5 | 5.3 | -5.4 | -78.3% | 3.8 | 253.3% | -1.6 | -23.2% |
| 19.1 | *** | 23.8 | *** | *** | *** | *** | 4.7 | 24.6% |
| | Mean Increase: | | * | * | 2.9 pg/mL | 116.8% | 8.9 pg/mL | 38% |
| | Mean Decrease: | | -9.9 pg/mL | -50.9% | -2.7 pg/mL | -25.5% | -10.1 pg/mL | -41.8% |

*Only 1 participant met this criterion
***Participant unavailable

TABLE 5

Female DHEAS Levels
DHEAS

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 4.4 | 5.5 | 7.2 | 1.1 | 24.9% | 1.7 | 30.9% | 2.8 | 63.6% |
| 12.2 | 13.0 | 9.5 | 0.8 | 6.5% | -3.5 | -26.9% | -2.7 | -22.1% |

TABLE 5-continued

Female DHEAS Levels
DHEAS

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 1.3 | 1.4 | 0.7 | 0.1 | 7.7% | −0.7 | −50.0% | −0.6 | −46.2% |
| 5.2 | 2.8 | 3.5 | −2.4* | −46.2%* | 0.7 | 25.0% | −1.7 | −32.7% |
| 6.7 | 7.5 | 8.8 | 0.8 | 11.9% | 1.3 | 17.3% | 2.1 | 31.3% |
| 7.6 | 8.8 | 5.6 | 1.2 | 15.8% | −3.2 | −36.4% | −2.0 | −26.3% |
| 9.5 | 20.7 | 12.5 | 11.2 | 117.9% | −8.2 | −39.6% | 3.0 | 31.6% |
| 13.2 | 16.2 | 11.1 | 3.0 | 22.7% | −5.1 | −31.5% | −2.1 | −15.9% |
| | Mean Increase: | | 2.6 pg/mL | 29.6% | 1.3 pg/mL | 24.4% | 2.6 pg/mL | 42.2% |
| | Mean Decrease: | | * | * | −4.1 pg/mL | −36.9% | −1.8 pg/mL | −28.6% |

*Only 1 participant met this criterion

Example 3

Testosterone

Testosterone is the primary sex hormone in the male body. However, it is also present and needed in the female body for the same process, just in lesser quantities. Testosterone is responsible for the changes that come on around puberty in men such as the voice lowering, enlargement of the penis and testes and hair growth. It is also the key hormone behind the male libido, or the desire to have sex. In women, it is largely responsible for enhancing the female libido and sexual function. Testosterone can be made in three different places. For men, most of the testosterone is made in the testicles. For men and women, small amounts of testosterone can be made by the adrenal glands. For women only, small amounts can also be made in the ovaries.

Testosterone production starts with signals that are transported from the pituitary gland and the hypothalamus. The hypothalamus produces a hormone called gonadotropin. This hormone transmits to the pituitary gland, which is then stimulated to produce follicle-stimulating hormones. These hormones run from the pituitary gland to the testicles and tell the testes to produce testosterone. The brain is then able to sense when the body has enough or has too much testosterone and regulates its production through the pituitary gland. Elevated cortisol associated with stress may cause a shortage of testosterone in the body. Not getting enough testosterone for men can mean a decreased sex drive and erectile dysfunction. In women, it can result in a lowered libido.

In this study, men under age 50 experienced a 48.9% testosterone increase after 60 days and women experienced a 48.8% testosterone increase during the 30-day supplementation with spermine and spermidine. (Table 6, 7).

TABLE 6

Male Testosterone Levels
Testosterone

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 72.0 | 92.0 | 100.0 | 20.0 | 27.7% | 8.0 | 8.7% | 28.0 | 38.8% |
| 55.0 | 52.0 | 101.0 | −3.0 | −5.5% | 49.0 | 94.2% | 46.0 | 83.6% |
| 62.0** | 65.0 | 56.0 | 3.0 | 4.8% | −9.0 | −13.8% | −6.0 | −9.7% |
| 75.0** | 50.0 | 35.0 | −25.0 | −33.3% | −15.0 | −30.0% | −40.0 | −53.3% |
| 88.0** | 58.0 | 59.0 | −30.0 | −34.1% | 1.0 | 1.7% | −29.0 | −32.9% |
| 105.0** | 31.0 | 52.0 | −74.0 | −70.5% | 21.0 | 67.7% | −53.0 | −50.5% |
| 45.0 | *** | 56.0 | *** | *** | *** | *** | 11.0 | 24.4% |
| | Mean Increase: | | 11.5 pg/mL | 16.3% | 19.8 pg/mL | 43.1% | 28.3 pg/mL | 48.9% |
| | Mean Decrease: | | −33 pg/mL | −35.9% | −12 pg/mL | −21.9% | −32 pg/mL | −36.6% |

***Participant unavailable

TABLE 7

Female Testosterone Levels
Testosterone

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 34.0 | 39.0 | 31.0 | 5.0 | 14.7% | −8.0 | −20.5% | −3.0 | −8.8% |
| 26.0 | 40.0 | 34.0 | 14.0 | 53.8% | −6.0 | −15.0% | 8.0 | 30.8% |
| 18.0 | 27.0 | 13.0 | 9.0 | 50.0% | −14.0 | −51.9% | −5.0 | −27.7% |
| 36.0 | 16.0 | 12.0 | −20.0 | −55.5% | −4.0 | −25.0% | −24.0 | −66.6% |
| 31.0 | 38.0 | 39.0 | 7.0 | 22.6% | 1.0* | 2.6%* | 8.0 | 25.8% |
| 46.0 | 39.0 | 22.0 | −7.0 | −15.2% | −17.0 | −43.6% | −24.0 | −52.1% |
| 17.0 | 35.0 | 21.0 | 18.0 | 105.8% | −14.0 | −40.0% | 4.0 | 23.5% |
| 24.0 | 35.0 | 35.0 | 11.0 | 45.8% | 0.0 | 0.0% | 11.0 | 45.8% |
| Mean Increase: | | | 10.6 pg/mL | 48.8% | * | * | 7.8 pg/mL | 31.5% |
| Mean Decrease: | | | −13.5 pg/mL | −35.4% | −10.5 pg/mL | −32.6% | −14 pg/mL | −38.8% |

*Only 1 participant met this criterion

Example 4

Progesterone

Progesterone is secreted by the empty egg follicle after ovulation has occurred, known as the corpus luteum. It is highest during the last phases of the menstrual cycle, after ovulation. Progesterone causes the endometrium to secrete special proteins to prepare it for the implantation of a fertilized egg. When fertilization does not occur, it prevents the body from creating and releasing more eggs in the later stages of the menstrual cycle.

If conception has occurred, progesterone becomes the major hormone supporting pregnancy, with many important functions. It is responsible for the growth and maintenance of the endometrium. It also suppresses further maturation of eggs by preventing release of luteinizing hormone (LH) and follicle stimulating hormone (FSH). By relaxing the major muscle of the uterus, progesterone prevents early contractions and birth. It does, however, also thicken the muscle helping the body prepare for the hard work of labor. Finally, progesterone suppresses prolactin (the primary hormone of milk production), preventing lactation until birth.

Progesterone is a female hormone used for reproduction but it is also found in men. While progesterone still largely functions as a female reproduction facilitator, it can also be beneficial to men suffering from benign prostatic hyperplasia or an enlarged prostate. Men produce about half as much progesterone as women. They use it to make testosterone, the main male hormone, and produce cortisone, a hormone produced by the adrenal glands (see FIG. 1).

The prostate is a gland a little larger than a walnut that wraps around the urethra just under the bladder. It helps the fertilization process by producing a fluid filled with nutrients that mixes with the sperm to form semen and helps the sperm survive in the vagina's environment. The prostate experiences a growth spurt from male puberty to about the age of 20. It begins to grow again during a man's 40's as a natural part of aging. This is called benign prostatic hyperplasia and most men will have it by their 50's and 60s'.

Men produce both testosterone and estrogen, another female hormone. The ratio of testosterone to estrogen is very high in a healthy man, but as men age that ratio can change. Many scientists believe that this is what causes the growth of the prostate as men age. Progesterone counteracts the effects of estrogen in men and improves the testosterone/estrogen ratios. It prevents testosterone from being converted into dihydrotestosterone (DHT), a weaker version of testosterone that dilutes the male hormone ratio.

In this study, 100% of men achieved an average decrease of 11.0 pg/mL (46.3%) in progesterone levels at 30 days and 85.7% maintained an average decrease of 10.0 pg/mL (37.2%) in progesterone levels at 60 days. One hundred percent of women with a decrease of progesterone levels at 30 days were either post-menopausal or in the luteal phase of the menstrual cycle. These levels remained lower than baseline at 60 days. On average, progesterone levels decreased 22.8 pg/mL. However, 100% of women with an increase of progesterone levels at 30 days were in the follicular phase of menstruation. These levels remained higher than baseline at 60 days. On average, progesterone levels increased 32.0 pg/mL.

TABLE 8

Male Progesterone Levels
Progesterone

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 22.0 | 18.0 | 13.0 | −4.0 | −18.2% | −5.0 | −27.7% | −9.0 | −40.9% |
| 20.0 | 9.0 | 19.0 | −11.0 | −55.0% | 10.0 | 111.1% | −1.0 | −5.0% |

TABLE 8-continued

Male Progesterone Levels
Progesterone

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 16.0 | 12.0 | 15.0 | −4.0 | −25.0% | 3.0 | 25.0% | −1.0 | −6.3% |
| 33.0 | 12.0 | 7.0 | −21.0 | −63.6% | −5.0 | −41.6% | −26.0 | −78.8% |
| 21.0 | 5.0 | 26.0 | −16.0 | −76.2% | 21.0 | 420.0% | 5.0 | 23.8% |
| 25.0 | 15.0 | 15.0 | −10.0 | −40.0% | 0.0 | 0.0 | −10.0 | −40.0% |
| 25.0 | *** | 12.0 | *** | *** | *** | *** | −13.0 | −52.0% |
| | Mean Increase: | | −11.0 pg/mL | −46.3% | −5 pg/mL | −34.70% | −10.0 pg/mL | −37.2% |
| | Mean Decrease: | | **** | **** | 11.3 pg/mL | 185.4% | * | * |

*Only 1 participant met this criterion
***Participant unavailable
****No participants met this criterion

TABLE 9

Female Progesterone Levels
Progesterone

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 57.0 | 132.0 | 110.0 | 75.0 | 131.6% | −22.0 | −16.6% | 53.0 | 92.9% |
| 52.0 | 42.0 | 35.0 | −10.0 | −19.2% | −7.0 | −16.6% | −17.0 | −32.7% |
| 21.0 | 72.0 | 83.0 | 51.0 | 242.9% | 11.0 | 15.3% | 62.0 | 295.2% |
| 37.0 | 8.0 | 11.0 | −29.0 | −78.4% | 3.0 | 37.5% | −26.0 | −70.3% |
| 23.0 | 21.0 | 14.0 | −2.0 | −8.7% | −7.0 | −33.3% | −9.0 | −39.1% |
| 48.0 | 9.0 | 9.0 | −39.0 | −81.2% | 0.0 | 0.0% | −39.0 | −81.2% |
| 38.0 | 49.0 | 44.0 | 11.0 | 38.9% | −5.0 | −10.2% | 6.0 | 15.8% |
| 16.0 | 16.0 | 23.0 | 0.0 | 0.0% | 7.0 | 43.8% | 7.0 | 43.8% |
| | Mean Increase: | | −20.0 pg/mL | −46.9% | −10.3 pg/mL | −19.2% | −22.8 pg/mL | −55.8% |
| | Mean Decrease: | | 45.7 pg/mL | 137.8% | 7 pg/mL | −32.2% | 32.0 pg/mL | 111.9% |

Example 5

Estradiol

Estradiol is the form of estrogen produced by the ovary, and is what is measured during routine infertility monitoring.

Estrogen is a group of hormones that are known best for their role in changing a girl into a woman with child-bearing potential. Estrogen also helps regulate the menstrual cycle, protects bones from thinning, and keeps cholesterol levels low to protect the heart. Estrogen can sometimes help turn normal breast tissue into cancers. Estrogen is made in three ways: within your body, in nature, and in a synthetic form used in medications.

Estrogen, like any other hormone, can be both beneficial and harmful. Research has shown that a few chemicals, called estrogenic xenobiotics, can mimic estrogen in the body and cause health problems the same way that excessive estrogen might do naturally. For example, the chemical nonylphenol, found in cleaning products, paints, herbicides, and pesticides, can damage human sperm.

Many medicinal and edible plants contain compounds called phytoestrogens, which are chemically similar to the sex hormone estradiol, the primary estrogen in humans. Although it is generally regarded as a "woman's hormone," estradiol also occurs naturally in a man's body (it is produced in the testes). In addition, as in a woman's body, a man's body produces precursor hormones (including testosterone), which are converted to estradiol. (Table 1). In a man's body, estradiol is involved in sexual functioning, the synthesis of bone, cognitive functioning, and the modulation of several diseases (including cancer and heart disease).

In this study, 83% of men experienced a 55.9% decrease in estradiol in 30 days. This indicates that spermine and spermidine may be potent estrogen-blocking supplements. 50% of women experienced an increase in Estradiol during the 30-day supplementation with spermine and spermidine, 75% of these also experiencing a concomitant increase in progesterone. Once the supplement was withdrawn the levels of estradiol began to decline among women and increase in men. (Table 10, 11).

TABLE 10

Male Estradiol Levels
Estradiol

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 2.4 | 1.0 | 1.0 | -1.4 | -58.3% | 0.0 | 0.0 | -1.4 | -58.3% |
| 1.7 | 0.5 | 2.7 | -1.2 | -70.6% | 2.2 | 440.0% | 1.0 | 58.8% |
| 1.2 | 0.8 | 1.5 | -0.4 | -33.3% | 0.7 | 87.5% | 0.3 | 25.0% |
| 3.3 | 7.7 | 3.4 | 4.4* | 133.3%* | -4.3* | -55.8%* | 0.1 | 3.0% |
| 1.2 | 0.5 | 0.8 | -0.7 | -58.3% | 0.3 | 60.0% | -0.4 | -33.3% |
| 1.7 | 0.7 | 1.8 | -1.0 | -58.8% | 1.1 | 157.1% | 0.1 | 5.9% |
| 1.6 | *** | 1.5 | *** | *** | *** | *** | -0.1 | -6.3% |
| | Mean Increase: | | -0.9 pg/mL | -55.9% | * | * | -0.6 pg/mL | -32.6% |
| | Mean Decrease: | | * | * | 1.1 pg/mL | 148.9% | 0.4 pg/mL | 23.2% |

*Only 1 participant met this criterion
***Participant unavailable

TABLE 11

Female Estradiol Levels
Estradiol

| Participant Baseline Levels pg/mL | Participant Treatment Levels (at 30 days) pg/mL | Participant Post-Treatment Levels (at 60 days) pg/mL | Baseline vs. Treatment pg/mL | % | Treatment vs. Post-Treatment pg/mL | % | Baseline vs. Post-Treatment pg/mL | % |
|---|---|---|---|---|---|---|---|---|
| 1.7 | 2.9 | 1.6 | 1.2 | 70.6% | -1.3 | -44.8% | -0.1 | -5.8% |
| 3.5 | 2.5 | 2.9 | -1.0 | -28.6% | 0.4 | 15.9% | -0.6 | -17.1% |
| 0.8 | 1.1 | 1.4 | 0.3 | 37.5% | 0.3 | 27.3% | 0.6* | 74.9%* |
| 1.3 | 0.6 | 0.8 | -0.7 | -53.8% | 0.2 | 33.3% | -0.5 | -38.5% |
| 1.7 | 0.9 | 0.6 | -0.8 | -47.0% | -0.3 | -33.3% | -1.1 | -64.7% |
| 3.1 | 3.4 | 2.0 | 0.3 | 9.7% | -1.4 | -41.2% | -1.1 | -35.5% |
| 2.4 | 3.1 | 1.9 | 0.7 | 29.2% | -1.2 | -38.7% | -0.5 | -20.8% |
| 1.7 | 1.5 | 1.5 | -0.2 | -11.8% | 0.0 | 0.0% | -0.2 | -11.8% |
| | Mean Increase: | | 0.6 pg/mL | 36.8% | 0.3 pg/mL | 25.5% | * | * |
| | Mean Decrease: | | -0.7 pg/mL | -35.3% | -1.0 pg/mL | -39.5% | -0.6 pg/mL | -27.7% |

*Only 1 participant met this criterion

As shown through the above studies, spermine and spermidine, the biogenic polyamines found in food and produced endogenously from the amino acids ornithine and methionine, reduce cortisol levels in men and women, opening the way for improved sexual function and fertility. Further, they decrease estradiol in men, potentially negating some of the loss of sexual function associated with estrogen dominance. Spermine and spermidine also improve the estrogen levels in some women and also improve the estrogen to progesterone ratio, again, potentially reducing the negative effects of estrogen dominance. Furthermore, spermine and spermidine improve testosterone levels in men under age 50 and increase DHEAS levels in men over age 50, both markers correlated with improved sexual function.

Women who experienced non-disabling mood swings and irritability associated with hormone fluctuations demonstrated a significant reduction in symptoms (80%) after only 30 days on spermine/spermidine supplementation. Further, women who experience low back and hip pain associated with hormone fluctuations demonstrated a significant reduction in symptoms (80%) after only 30 days on spermine/ spermidine supplementation. Men likewise experienced reduction in pain or fatigue in the legs or back (62%).

Men experiencing low energy level or stamina realized a 50% improvement in symptoms and women experiencing unusual fatigue realized a 75% improvement in symptoms after only 30 days on spermine/spermidine supplementation.

Finally, among men experiencing a sense of bladder fullness and frequent or urgent need to urinate, fully 55% demonstrated a significant reduction in symptoms after only 30 days on spermine/spermidine supplementation. And women experiencing urinary difficulties found their symptoms we relieved (66%) after only 30 days on spermine/spermidine supplementation.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public.

REFERENCES CITED

Several references have been described in this patent specification. A full citation is presented below and the contents of the cited references are incorporated by reference herein.

Brant, Samuel J. and Ryczek, Shelli, J., The Regulatory Effect of Biogenic Polyamines Spermine and Spermidine in Men and Women (2011).

Groppa, M D and Benavides, M P, POLYAMINES AND ABIOTIC STRESS: RECENT ADVANCES, Amino Acids 2008 January, 34(1):35-45. Epub 2007 Mar. 14. Departamento de Química Biológica, Facultad de Farmacia y Bioquímica, Universidad de Buenos Aires, Buenos Aires, Argentina.

Bardocz S, Duguid T J, Brown D S, Grant G, Pusztai A, White A, et al. The importance of dietary polyamines in cell regeneration and growth. Br J Nutr. 1995; p. 73:819-28.

Loser C. Polyamines in human and animal milk. Br J Nutr. 2000; p. 84:S55-8.

Tabor C W, Tabor H. Polyamines. Annu Rev Biochem. 1984; p. 53:749-90.

Loser C, Folsch U R. Importance of various intracellular regulatory mechanisms of polyamine metabolism in camostate-induced pancreatic growth in rats. Digestion. 1993; p. 54:213-23.

Williams-Ashman, H. G. and Lockwood, D. H. (1970) ROLE OF POLYAMINES IN REPRODUCTIVE PHYSIOLOGY AND SEX HORMONE ACTION. Annals of the New York Academy of Sciences, 171:882-894. doi: 10.1111/j.1749-6632.1970.tb39395.x Loser C, Eisel A, Harms D, Folsch U R. Dietary polyamines are essential luminal growth factors for small intestinal and colonic mucosal growth and development. Gut. 1999; p. 44:12-6.

Canellakis Z N, Marsh L L, Bondy P K. Polyamines and their derivatives as modulators in growth and differentiation. Yale J Biol Med. 1989; p. 62:481-91.

Seidel E R, Scemama J L. Gastrointestinal polyamines and regulation of mucosal growth and function. J Nutr Biochem. 1997; p. 8:104-11.

Kalac P, Krausova P. A review of dietary polyamines: formation, implications for growth and health and occurrence in foods. Food Chem. 2004; p. 90:219-30.

Dandrifosse G, Peulen O, El Khefif N, Deloyer P, Dandrifosse A C, Grandfils C. Are milk polyamines preventive agents against food allergy? Proc Nutr Soc. 2000; p. 59:81-6.

Dufour C, Dandrifosse G, Forget P, Vermesse F, Romain N, Lepoint P. Spermine and spermidine induce intestinal maturation in the rat. Gastroenterology. 1988; p. 95:112-6.

Bardocz S. Polyamines in food and their consequences for food quality and human health. Trends Food Sci Technol. 1995; p. 6:341-6.

Lovaas E, Carlin G. Spermine: an anti-oxidant and anti-inflammatory agent. Free Radic Biol Med. 1991; p. 11:455-61.

Exton M S, Bindert A, Kruger T, Scheller F, Hartmann U, Schedlowki M. Cardiovascular and endocrine alterations after masturbation-induced orgasm in women. Psychosom Med 1999; p. 61:280-9.

Exton N G, Truong T C, Exton M S, Wingenfeld S A, Leygraf N, Sailer B, Hartmann U, Schedlowski M. Neuroendocrine response to film-induced sexual arousal in men and women. Psychoneuroendocrinology 2000; p. 25:187-99.

Heiman J R, Rowland D L, Hatch J P, Gladue B A. Psychophysiological and endocrine responses to sexual arousal in women. Arch Sex Behav 1991; p. 20:171-86.

Larque E, Sabater-Molina M, Zamora S. Biological significance of dietary polyamines. Nutrition (New York, N.Y., United States) 2007; p. 23:87-95.

Eliassen K A, Reistad R, Risoen U, Ronning H F. Dietary polyamines. Food Chem. 2002; p. 78:273-80.

Igarashi K, Kashiwagi K. Polyamines: mysterious modulators of cellular functions. Biochem Biophys Res Commun. 2000; p. 271:559-64.

Deloyer P, Peulen O, Dandrifosse G. Dietary polyamines and non-neoplastic growth and disease. Eur J Gastroenterol Hepatol. 2001; p. 13:1027-32.

Colandra, R. S. et al. Physio Pharmaco Ther Latinoan, 1996; 45(4): 209-22

Dunshea and King, Br J Nutr, 73:819-828, June 1995

What is claimed is:

1. A method of treating a human male experiencing estrogen dominance comprising the steps of:
   identifying a level of at least one hormone in the human that is causing the estrogen dominance, wherein the at least one hormone is selected from the group consisting of cortisol, dehydroepiandrosterone sulfate, testosterone, progesterone, and estradiol;
   providing a composition that comprises between approximately 2.5 mg and 2.7 mg spermine and between approximately 2.5 mg and 2.7 mg spermidine;
   administering the composition to the human daily for a period of at least thirty days;
   modifying the level of the at least one hormone in order to decrease production of estrogen in the human; and
   decreasing progesterone levels in the human after thirty days of treatment.

2. The method of claim 1 further comprising the step of administering the composition to the human at least once daily.

3. The method of claim 1 further comprising the step of administering the composition to the human for a period between thirty days and sixty days.

4. The method of claim 1 further comprising the step of reducing cortisol levels in the human after thirty days of treatment.

5. The method of claim 1 further comprising the step of decreasing estradiol levels in the human after thirty days of treatment.

6. A method for treating hormonal imbalance in a human male, the method comprising the steps of:
   identifying a level of at least one hormone in the human, wherein the at least one hormone is selected from the group consisting of cortisol, dehydroepiandrosterone sulfate, testosterone, progesterone, and estradiol;
   identifying an imbalance of the at least one hormone in the human;
   administering a composition at least once daily to the human consisting of between approximately 2.5 mg and 2.7 mg spermine and between approximately 2.5 mg and 2.7 mg spermidine for a period of at least thirty days;

modifying the level of the at least one hormone that is imbalanced and decreasing progesterone levels in the human after thirty days of treatment.

7. The method of claim 6 further comprising the step of reducing cortisol levels in the human after thirty days of treatment.

8. The method of claim 6 further comprising the step of decreasing estradiol levels in the human after thirty days of treatment.

9. A method of treating a human male experiencing estrogen dominance comprising the steps of:

identifying a level of at least one hormone in the human that is causing the estrogen dominance, wherein the at least one hormone is selected from the group consisting of cortisol, dehydroepiandrosterone sulfate, testosterone, progesterone, and estradiol;

providing a composition that comprises between approximately 2.5 mg and 2.7 mg spermine and between approximately 2.5 mg and 2.7 mg spermidine;

administering the composition to the human daily for a period of at least thirty days;

modifying the level of the at least one hormone in order to decrease production of estrogen in the human; and reducing cortisol levels in the human after thirty days of treatment.

10. A method of treating a human male experiencing estrogen dominance comprising the steps of:

identifying a level of at least one hormone in the human that is causing the estrogen dominance, wherein the at least one hormone is selected from the group consisting of cortisol, dehydroepiandrosterone sulfate, testosterone, progesterone, and estradiol;

providing a composition that comprises between approximately 2.5 mg and 2.7 mg spermine and between approximately 2.5 mg and 2.7 mg spermidine;

administering the composition to the human daily for a period of at least thirty days;

modifying the level of the at least one hormone in order to decrease production of estrogen in the human; and decreasing estradiol levels in the human after thirty days of treatment.

11. A method of treating a human female experiencing estrogen dominance comprising the steps of: identifying a level of at least one hormone in the human that is causing the estrogen dominance, wherein the at least one hormone is selected from the group consisting of cortisol, dehydroepiandorsterone sulfate, testosterone, progesterone, and estradiol; providing a composition that comprises between approximately 2.5 mg and 2.7 mg spermine and between approximately 2.5 mg and 2.7 mg spermidine; administering the composition to the human daily for a period of at least thirty days; modifying the level of the at least one hormone in order to decrease production of estrogen in the human; and increasing dehydroepiandrosterone sulfate levels in the human after thirty days of treatment.

12. A method of treating hormonal imbalance in a human female, the method comprising the steps of: identifying a level of at least one hormone in the human, wherein the at least hormone is selected from the group consisting of cortisol, dehydroepiandrosterone sulfate, testosterone, progesterone, and estradiol; identifying an imbalance of the at least one hormone in the human; administering a composition at least once daily to the human consisting of between approximately 2.5 mg and 2.7 mg spermine and between approximately 2.5 mg and 2.7 mg spermidine for a period of at least thirty days; modifying the level of the at least one hormone that is imbalanced; and increasing dehydroepiandrosterone sulfate levels in the human after thirty days of treatment.

* * * * *